Sept. 17, 1974 F. W. ANDERSON Plant Pat. 3,619
NECTARINE TREE
Filed Aug. 30, 1973
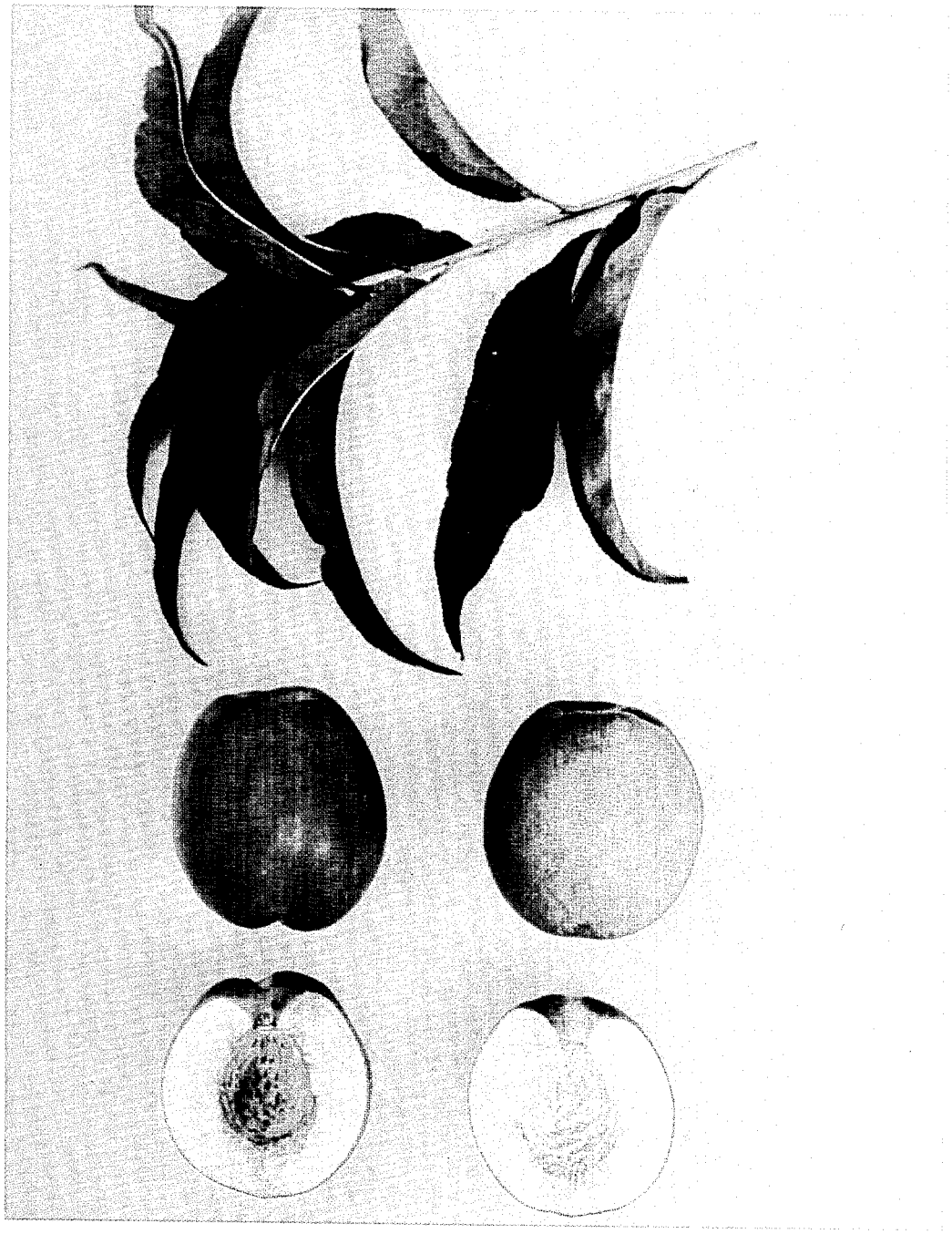

United States Patent Office

Plant Pat. 3,619
Patented Sept. 17, 1974

3,619
NECTARINE TREE

Frederic W. Anderson, Merced, Calif., assignor to
Reedley Nursery, Inc., Reedley, Calif.

Filed Aug. 30, 1973, Ser. No. 393,223
Int. Cl. A01h 5/03
U.S. Cl. Plt.—41 1 Claim

ABSTRACT OF THE DISCLOSURE

A nectarine tree which is large, vigorous, spreading, foliated with medium size, lanceolate leaves having a crenate margin, and a regular and productive bearer of uniform, medium size, symmetrical, globose-to-oblong, freestone fruit having yellow skin substantially entirely overspread with red at maturity, and yellow flesh.

*Background of the variety:* Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety:* The present variety of nectarine tree was originated by me, in my aforesaid experimental nursery and orchard, as an open-pollinated seedling of the Summer Grand nectarine (U.S. Plant Pat. No. 2,879).

*Asexual repoduction of the variety:* Subsequent to origination by me of the present variety of nectarine tree, I asexually reproduced such variety by grafting it on mature orchard trees in my said experimental orchard. Such reproductions ran true to the original tree in all respects.

*Summary of the variety:* The present variety of nectarine tree is large, vigorous, spreading, foliated with medium size, lanceolate leaves having a crenate margin, and a regular and productive bearer of uniform, medium size, symmetrical, globose-to-oblong, freestone fruit having yellow skin substantially entirely overspread with red at maturity, and yellow flesh; the variety—which generally resembles the seed parent, Summer Grand—being characteristically distinct by bearing fruit which ripens approximately two weeks earlier than the Summer Grand, and in the interim between ripening of the May Grand (U.S. Plant Pat. No. 2,794) and the Early Sun Grand (U.S. Plant Pat. No. 1,420).

*Brief description of the drawing:* The drawing is an illustration, by photographic reproduction in color, of a twig with leaves, and separate fruit; one of the latter being cut in half to expose the flesh, and the stone remaining in one of the halves.

*Description of the variety:* The botanical details of this new and distinct variety of nectarine tree—with color definitions referenced to Maerz and Paul Dictionary of Color—are as follows:

Tree:
- *Size.*—Large.
- *Vigor.*—Vigorous.
- *Growth.*—Spreading.
- *Production*—Productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.*—Medium. Average length—6½". Average Width—¾".
- *Form.*—Lanceolate. Acutely pointed.
- *Thickness.*—Medium.
- *Margin.*—Crenate.
- *Petiole.*—Medium length. Medium thickness.
- *Glands.*—Average number—4. Alternate. Medium size. Reniform. Usually positioned 2 on petiole and 2 on leaf blade.
- *Color.*—Top side—Medium green (22–L–8). Under side—Lighter green (21–J–7).

Flower buds:
- *Size.*—Large to medium.

Flowers:
- *Blooming Period.*—About with Sun Grand nectarine (U.S. Plant Pat. No. 974). Medium, as compared with other varieties.

Fruit:
- *Maturity When Described.*—Eating ripe—July 5th, 1973.
- *Date of First Picking.*—June 20th, 1973.
- *Date of Last Picking.*—June 30th, 1973.
- *Size.*—Uniform. Medium. Average diameter axially—2⅜". Average transversely in suture plane—2 5/16".
- *Form.*—Uniform. Symmetrical. Globose to oblong.
- *Suture.*—Shallow. Extends from base to beyond apex.
- *Ventral Surface.*—Rounded.
- *Cavity.*—Rounded. Elongated in suture plane, with suture showing on one side.
- *Apex.*—Short. Depressed.
- *Pistil Point.*—Very small.

Skin:
- *Thickness.*—Medium.
- *Texture.*—Tough.
- *Tendency To Crack.*—None.
- *Down.*—Wanting.
- *Color.*—Yellow (10–L–6) substantially entirely overspread at maturity with red (5–L–8) shading darker to (7–L–6), with light streaking and mottling.

Flesh:
- *Texture.*—Firm. Meaty.
- *Fibers.*—Few.
- *Ripens.*—Evenly.
- *Flavor.*—Subacid. Vinuous.
- *Eating Quality.*—Good to best.
- *Color.*—Yellow (10–K–5) *Surface of pit cavity:*: Yellow (10–K–5) with some red (4–L–7); the red streaking slightly into flesh.

Stone:
- *Type.*—Free.
- *Size.*—Medium. Average length—1¼". Average breadth—1". Average thickness—⅞".
- *Form.*—Oblong. Obovoid.
- *Base.*—Straight.
- *Apex.*—Acute.
- *Sides.*—Equal.
- *Tendency To Split.*—Slight.
- *Color.*—Light tan (13–L–9).

Use: Market—local and long distance shipping. Dessert.
Keeping quality: Good.
Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, spreading, foliated with medium size, lanceolate leaves having a crenate margin, and a regular and productive bearer of uniform, medium size, symmetrical, globose-to-oblong, freestone fruit having yellow skin substantially entirely overspread with red at maturity, and yellow flesh; the variety—which generally resembles the seed parent, Summer Grand—being characteristically distinct by bearing fruit which ripens approximately two weeks earlier than the Summer Grand, and in the interim between ripening of the May Grand and the Early Sun Grand.

No references cited.

ROBERT E. BAGWILL, Primary Examiner